United States Patent [19]
Kroll

[11] Patent Number: 5,391,185
[45] Date of Patent: Feb. 21, 1995

[54] ATRIAL CARDIOVERTER WITH VENTRICULAR PROTECTION

[75] Inventor: Mark W. Kroll, Minnetonka, Minn.

[73] Assignee: Angeion Corporation, Plymouth, Minn.

[21] Appl. No.: 20,573

[22] Filed: Feb. 22, 1993

[51] Int. Cl.⁶ ............................................. A61N 1/39
[52] U.S. Cl. ...................................................... 607/4
[58] Field of Search ...................... 607/4, 5, 123, 122, 607/119, 116

[56] References Cited

U.S. PATENT DOCUMENTS

| | | | |
|---|---|---|---|
| 3,738,370 | 6/1973 | Charms | |
| 4,727,877 | 3/1988 | Kallok | |
| 5,014,696 | 5/1991 | Mehra | |
| 5,074,301 | 12/1991 | Gill | 607/4 |
| 5,107,834 | 4/1992 | Ideker et al. | 607/5 |
| 5,193,536 | 3/1993 | Mehra | 607/4 |
| 5,209,229 | 5/1993 | Gilli | 607/4 |
| 5,243,980 | 9/1993 | Mehra | 607/6 |
| 5,251,624 | 10/1993 | Bocek et al. | 607/6 |
| 5,265,600 | 11/1993 | Adams et al. | 607/4 |

FOREIGN PATENT DOCUMENTS 9218198 10/1992 WIPO ...................... 607/5

Primary Examiner—William E. Kamm
Assistant Examiner—Kennedy J. Schaetzle
Attorney, Agent, or Firm—Patterson & Keough

[57] ABSTRACT

A method and system for conducting atrial defibrillation of a patient while mitigating the rest of the defibrillation countershock to prevent unwanted ventricular fibrillation. The system comprises an atrial sensing electrode subsystem, an atrial defibrillation subsystem, a ventricular pacing electrode subsystem, a power source subsystem to provide atrial defibrillation, a power source subsystem to provide ventricular pacing discharge, and a control subsystem to synchronize atrial defibrillation discharge with ventricular pacing so that atrial defibrillation discharge occurs during the QRS phase of a ventricular contraction cycle.

4 Claims, 4 Drawing Sheets

ATRIAL CARDIOVERTER WITH VENTRICULAR PROTECTION

FIELD OF THE INVENTION

The present invention relates generally to implantable systems for control of atrial fibrillation and more particularly to a protection means to treat atrial fibrillation in synchronization with ventricular pacing such that a fibrillation countershock occurs during ventricular refractory periods.

BACKGROUND OF THE INVENTION

Atrial fibrillation is the rapid and asynchronous contraction of individual muscle fibers within the atria of the heart. One result of this fibrillation within the atrium is functional loss of the augmented pumping capability of the heart. Normally the atria operate in very low pressure states such that loss of atrial contraction will not lead to cessation of blood flow and death. During atrial fibrillation the blood continues to flow passively through the atria into the ventricles with only a 10-15% diminution of blood flow. Depending on total cardiac reserves and patient status, this diminution of cardiac output may or may not be symptomatic to the patient.

A second effect of atrial fibrillation is a rapid ventricular response. The classic clinical description is a rapid irregularly irregular heart rate. This irregular irregularity is caused by incomplete or partial conduction of the atrial fibrillation currents arriving at the AV node. The atrial fibrillation rates are extremely high and are usually not conducted on a one-to-one basis. Instead, as the AV node receives one signal and passes it on, the AV node enters a short refractory period during which it will not respond to any other subsequent atrial fibrillation. When the refractory period ends the AV node is again sensitive to atrial fibrillation currents. When the next fibrillation current arrives, the AV node responds by triggering the next ventricular contraction. Since there are far more atrial fibrillation currents the overall ventricular rate increases but is irregularly irregular due to the refractory periods of the conduction system.

This rise in the ventricular response rate also affects hemodynamic stability by decreasing diastolic filling times. The contraction time period for the ventricles during systole is generally the same length, regardless of pulse rate. Therefore, in order to increase pulse rate, then the time between successive systolic events, i.e., the diastolic period, must shorten. Since the only time available to the heart to refill the ventricles is during diastole, a decrease in this time period leads to a decrease in refilling the ventricles. The heart has less blood for the next contraction causing additional diminution of cardiac output.

A further complication secondary to this irregular rate is timing of the atrial defibrillation countershock. Studies have shown that although atrial defibrillation is a reliable treatment modality, in a few percent of the cases the atrial defibrillating countershock will cause fibrillation in the ventricles. The irregularly irregular ventricular rate forces a randomly timed countershock. If a defibrillation countershock to the atria inadvertently occurs during the T wave of the ventricular cycle, ventricular fibrillation may be precipitated. Ventricular fibrillation is life threatening and requires further immediate countershock therapy to the ventricles and therefore is best avoided.

An additional secondary effect of atrial fibrillation and the passive blood flow through the atrial chambers is formation of mural thrombi. Formation of these blood clots is generally avoided if atrial fibrillation is treated successfully within a time period ranging from minutes to several hours after onset. Once formed, these thrombi become sources of embolization to both the pulmonary as well as the systemic circulations. Embolization to the pulmonary vasculature leads to decreased oxygenation and carbon dioxide exchange within the lungs. Since all of the output of the right side of the heart circulates to the lungs, all clots embolized from the right atrium will lodge in the lungs. Death can ensue if the degree of embolization is severe enough. Embolization to the systemic vascular system leads to strokes if the embolus travels to the brain. Other organ injury occurs depending upon where the embolus stopped.

Ideally, the treatment of atrial fibrillation is performed in such a manner that there is reasonably prompt conversion of the atrial fibrillation back into an organized atrial contraction with subsequent capture of the ventricles. There are a number of atrial cardioverter/defibrillator systems which are known. These systems generally comprise either isolated atrial systems or are in combination with ventricular defibrillation systems. A number of electrode configurations are also disclosed in conjunction with the various systems.

SUMMARY OF THE INVENTION

The present invention discloses methods and apparatuses for conducting atrial defibrillation while mitigating the risk of the defibrillation countershock causing ventricular fibrillation. The present invention discloses means for an implantable atrial cardiovertery/defibrillator providing ventricular protection through use of a ventricular pacing pulse synchronized to an atrial defibrillation countershock electrical discharge.

The present invention comprises an implantable atrial cardioverter/defibrillator comprising: atrial dysrythmia detection means for determining the occurrence of atrial fibrillation; atrial countershock means for treating the occurrence of atrial dysrhythmia; ventricular pacing means for capturing and controlling the ventricular pulse; and control means for so that the countershock occurs in conjunction with the ventricular QRS phase. Furthermore, the invention utilizes a multiplicity of countershock electrodes and positions for these electrodes to provide optimum immersion of the atrial myocardium within the defibrillation countershock electrical field.

The above and other objects and advantages will become more readily apparent when reference is made to the following description taken in conjunction with the accompanying drawings.

DETAILED DESCRIPTION OF THE INVENTION

The present invention discloses a method and system for detecting atrial fibrillation, pacing the ventricles, and timing the atrial defibrillation countershock to coincide with the R wave of the QRS phase of the ventricular contraction cycle. Pacing of the ventricles in this fashion allows the system to anticipate ventricular contraction so as to avoid an atrial defibrillation countershock during the T wave of the ventricular contraction cycle. Without such protection, as the ventricles are allowed to beat at their irregularly irregular rate, an inadvertent atrial defibrillation countershock during the T wave can occur causing ventricular fibrillation.

Figure 1:
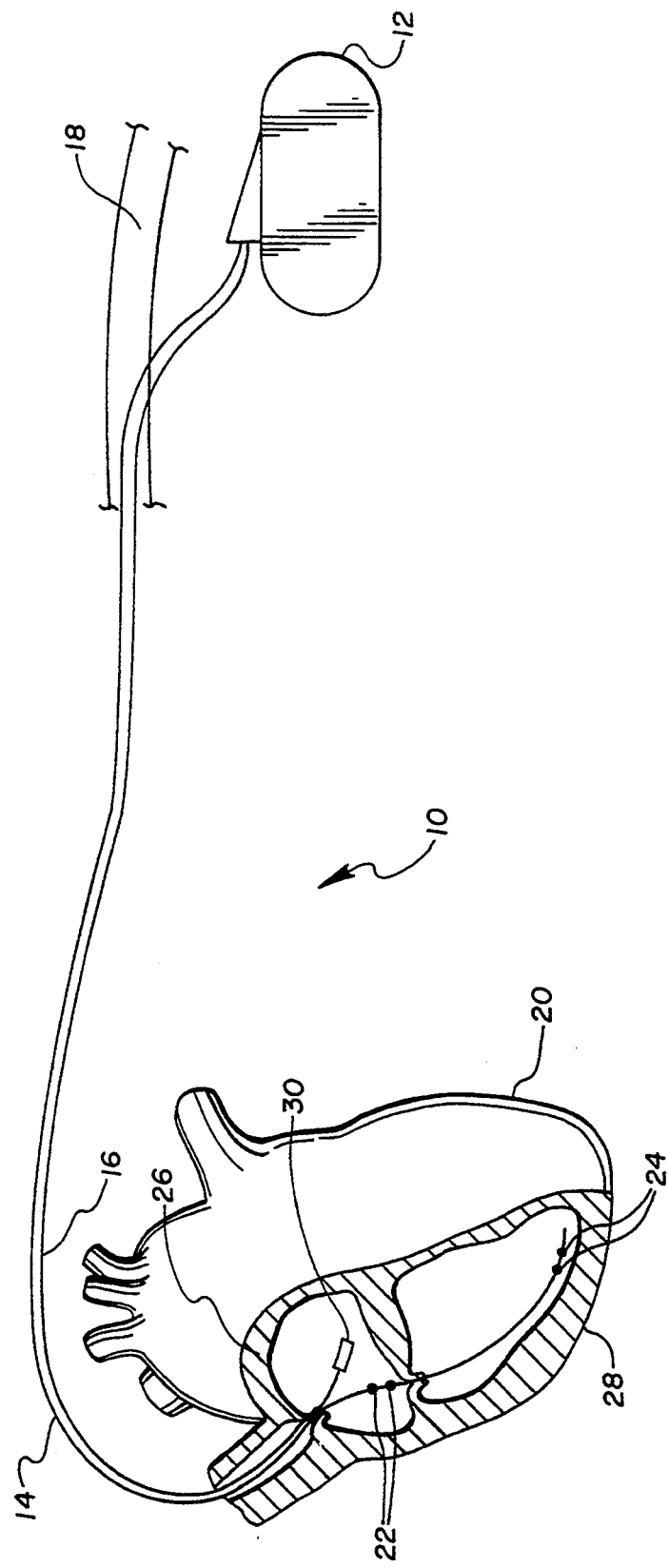
FIG. 1 is a schematic representation of a system embodiment depicting the pulse generator can, sensing and pacing electrodes, and defibrillation electrodes.

FIG. 1 discloses an embodiment for an atrial cardioverter defibrillator system 10. The pulse generator can 12 portion of system 10 comprises components for logic and timing of ventricular and atrial pulses, diagnostic paradigms to determine atrial fibrillation events, diagnostic paradigms to determine ventricular rate, output pacing circuits to drive the right ventricular pacing apparatus, and high voltage output circuits supplying the necessary defibrillation countershock to the atria. In addition, the outer housing surface of pulse generator can 12 also serves as a defibrillation discharge electrode. System 10 is completed with placement of a sensing-/pacing catheter 14 and atrial discharge catheter 16. System 10 is generally implanted within the subcutaneous space of a patient, in a position inferior to a clavicle providing convenient access to a subclavicular vein 18.

Catheters 14 and 16 traverse the venous vasculature to gain access to the right side of the heart 20. Catheter 14 positions sensing electrode complex 22 within right atrium 26 and pacing electrode complex 24 within right ventricle 28. As depicted, catheter 16 positions a right atrial defibrillation discharge electrode 30 within right atrium 26.

Figure 2:
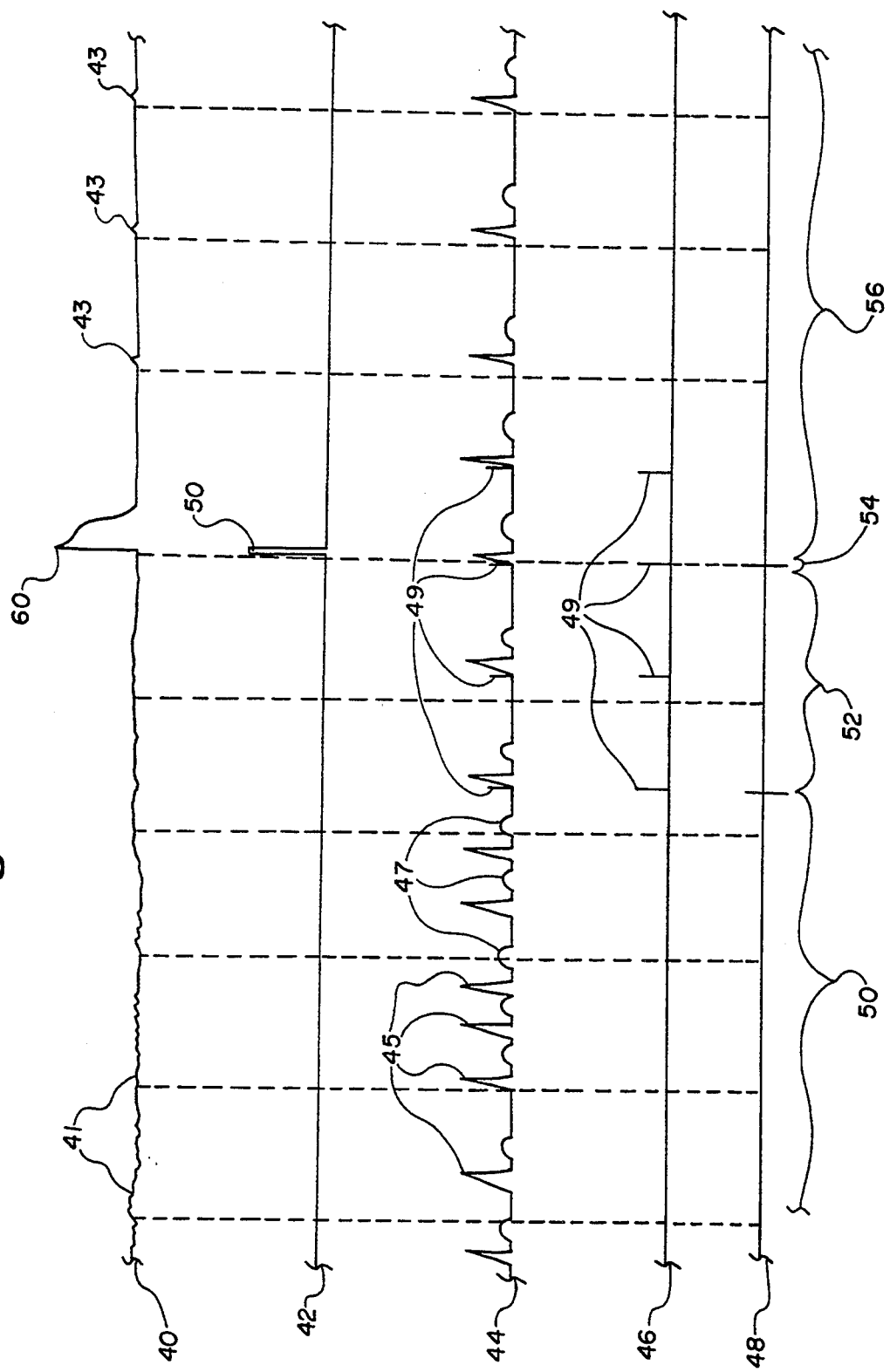
FIG. 2 is a time sequence of events carried out by the present invention depicted as various events occurring at different sites of the heart.

FIG. 2 depicts a time sequence representation of the invention's operation. Using FIG. 1 in conjunction with FIG. 2, right atrial sensing electrode complex 22 provides data to form a right atrial sensing tracing 40, the top tracing in FIG. 2. Right atrial defibrillation discharge electrode 30 of FIG. 1 provides data to form the corresponding atrial defibrillation discharge tracing 42 in FIG. 2. Right ventricular pacing electrode complex 24 of FIG. 1 provides data to form the third and fourth tracings in FIG. 2, a right ventricular pulse tracing 44 and a right ventricular pacing tracing 46. Tracings 40, 42, 44, and 46 share a common time line depicted in FIG. 2 as time line tracing 48. Time line 48 has been further divided into event periods 50, 52, 54, and 56 to correspond to invention function steps.

When atrial fibrillation occurs the atrial tracing reveals the fine irregular saw tooth effect 41, as depicted in tracing 40 of FIG. 2 during time period 50. The ventricular rate becomes rapid and irregularly irregular as shown in tracing 44 for time period 50, with each contraction noted by the depolarization QRS waves 45 and subsequent repolarization T waves 47. The invention then begins pacing of the ventricles as shown by pacing spikes 49 in tracings 44 and 46 during time period 52. With capture of the ventricles by the pacing function, the ventricular rate becomes regular and is equal to the pacing spike 49 rate as seen in time period 52 on tracing 44. Ventricular capture allows the invention to predict a ventricular contraction and the consequent QRS phase 45 which corresponds to time period 54. This time period 54 is timed with the third paced beat in tracing 44 as time period 52 merges into time period 54. An atrial defibrillation countershock 58 of tracing 42 is delivered to the atria during ventricular QRS phase 45 in time period 54. This countershock depolarizes atria 26 as shown in tracing 40 as signal 60. Defibrillation allows the atria to reorganize contraction represented by P waves 43 as shown in tracing 40 during time period 56. Ventricular pacing 49 is discontinued when the P waves 43 capture the ventricles as depicted in tracing 44 during time period 56.

Figure 3:
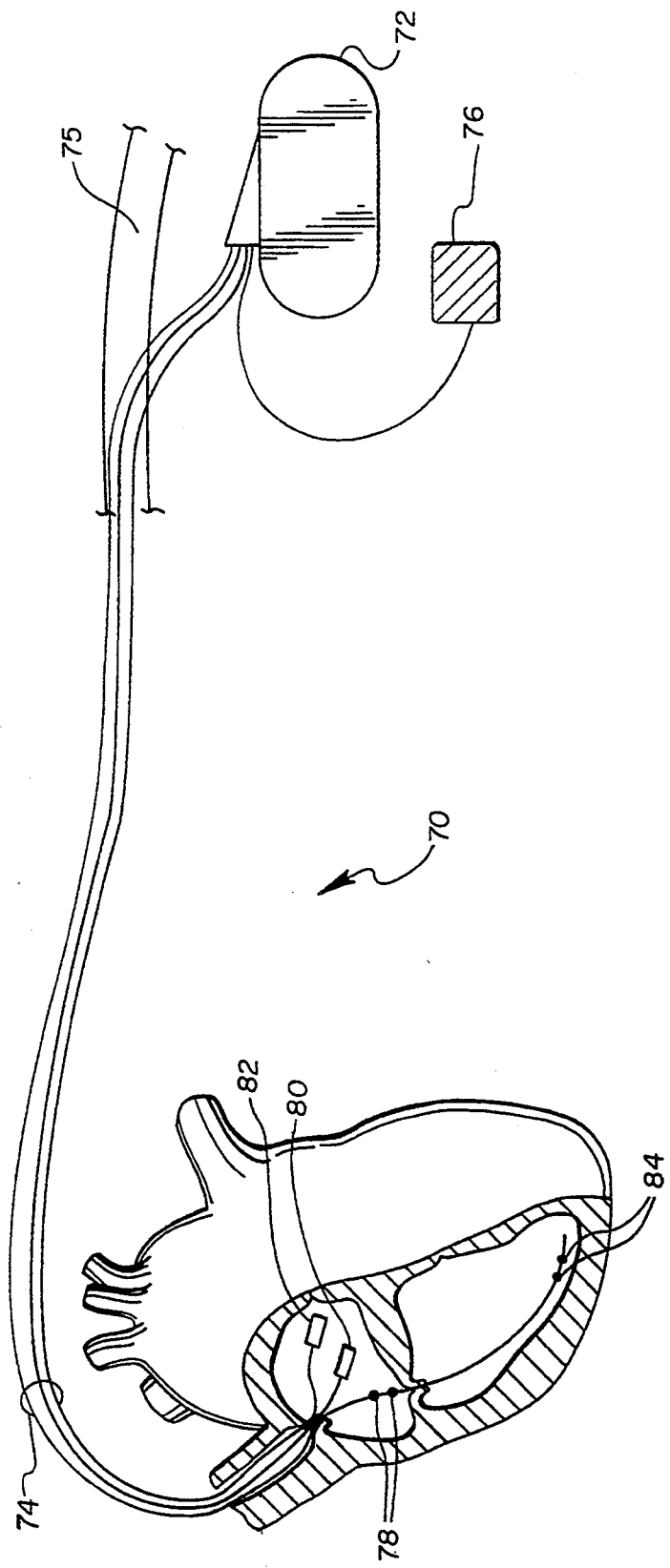
FIG. 3 is an additional schematic embodiment of the present invention depicting versatility in discharge electrode placement.

FIG. 3 is an alternative schematic representation of the invention. System 70 in FIG. 3 is similar to system 10 depicted in FIG. 1 in most respects. The notable difference is the number, and deployment of electrodes. System 70 is also intended to be implantable comprising: pulse generator can 72 housing control and power circuitry, with the housing surface of can 72 capable of acting as a discharge electrode; catheter bundle 74 with respective electrodes implanted via venipuncture; and a subcutaneous patch electrode 76 implanted in the subcutaneous space of the anterior chest wall proximate the heart. Catheter bundle 74 comprises right atrial sensing electrode complex 78, right atrial discharge electrode 80, right coronary sinus electrode 82 and right ventricular pacing electrode complex 84. In this system, right coronary sinus electrode 82 and subcutaneous electrode 76 provide additional electrodes for use in applying defibrillation countershock therapy.

The advantage in this electrode configuration for system 70 is the versatility in delivering the atrial defibrillation countershock. Co-pending U.S. patent application Ser. No. 07/841,544 discloses an optimal energy steering system utilizing multiple countershock discharge electrodes. Such a system provides for selection of various combinations of electrode sets to achieve desired immersion of the myocardium within the defibrillation electrical field. System 70 configuration consisting of a plurality of discharge electrodes allows for programming optimal energy steering. One or more electrodes can be chosen to act as anodes with any one or all of the remaining electrodes acting as cathodes. Based on the individual patient response, the electrode choice and pattern can be reprogrammed to optimize atrial defibrillation therapy.

Figure 4:
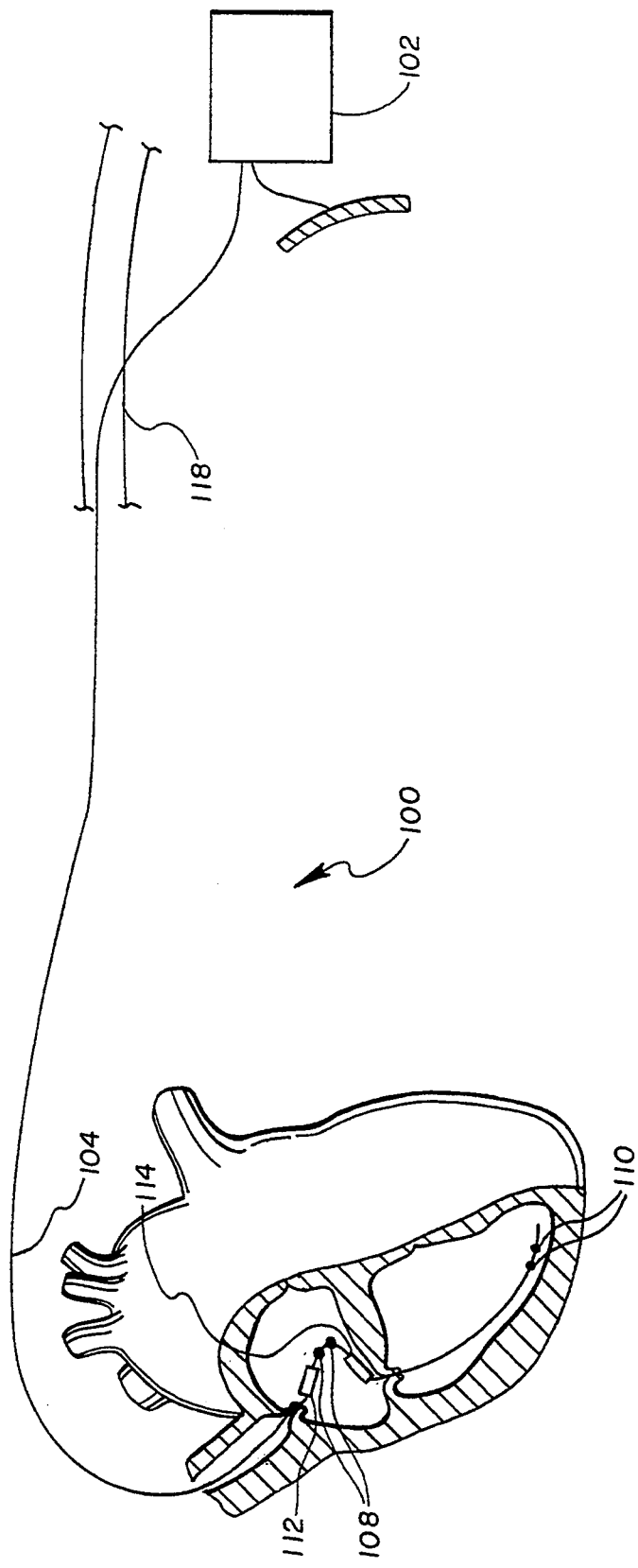
FIG. 4 is an additional schematic embodiment of the present invention depicting versatility in discharge electrode placement.

FIG. 4 discloses another embodiment of the invention. System 100 is comprised of similar components to system 10 in FIG. 1 and system 70 in FIG. 3. The significant differences in FIG. 4 are replacement of a pulse generator can with a bedside control and power unit 102, a single implantable catheter 104 and a skin patch electrode 106.

Catheter 104 carries multiple electrodes comprising a right atrial sensing electrode complex 108, a right ventricular pacing electrode complex 110, a proximal right atrial/superior vena cava discharge electrode 112 and a distal right atrial discharge electrode 114. Implantation is through vascular access 118 which may be subclavian or femoral veins.

The versatility of system 100 is in combining the ease of vascular access with a single catheter 104 and the bedside control and power unit 102 for use in urgent treatment of atrial fibrillation at the patient's bedside.

We claim:

1. An improved implantable atrial cardioverter for treating an atrial dysrhythmia of a human heart with cardioverting electrical energy, the cardioverter having atrial dysrhythmia detecting means for detecting an atrial dysrhythmia using a plurality of atrial sensing electrodes, pacing means for selectively providing pacing pulses to a plurality of ventricular pacing electrodes, charge storage means for selectively providing a cardioverting electrical energy to a plurality of implantable cardioversion discharge electrodes, and control means operatively connected to the detecting means, the pacing means and the charge storage means for selectively controlling the discharge of each, wherein the improvement comprises:

means within the control means for controlling the pacing means and the charge storage means such that upon detecting an atrial dysrhythmia the pacing means immediately begins providing pacing pulses to the ventricles and subsequently synchronizes the cardioverting electrical energy discharge of the charge storage means with the pacing pulses.

2. The cardioverter of claim 1 in which the atrial sensing means further comprises a means for detecting a sensed vetricular rate as part of the detection of an atrial dysrhythmia, and a means for signalling the control means to control the pacing means to pace at a rate higher than the sensed ventricular rate.

3. An improved method of atrial cardioversion for treating an atrial dysrhythmia of a human heart with cardioverting electrical energy, the cardioverter having atrial dysrhythmia detecting means for detecting an atrial dysrhythmia using a plurality of atrial sensing electrodes, pacing means for selectively providing pacing pulses to a plurality of ventricular pacing electrodes, charge storage means for selectively providing a cardioverting electrical energy to a plurality of implantable cardioversion discharge electrodes, and control means operatively connected to the detecting means, the pacing means and the charge storage means for selectively controlling the discharge of each, wherein the improved method comprises the cardioverter implemented steps of:

pacing the ventricles immediately upon a detection of an atrial dysrhythmia; and discharging the cardioverting electrical energy from the power storage means through the discharge electrodes in synchronization with the pacing of the ventricles.

4. The method of claim 3 further comprising the step of determining a sensed ventricular rate at the time of the detection of the atrial dysrhythmia; and pacing the ventricles at a rate higher than the sensed ventricular rate.

* * * * *